US011426546B2

(12) United States Patent
Russo et al.

(10) Patent No.: US 11,426,546 B2
(45) Date of Patent: Aug. 30, 2022

(54) MEDICAL VENTILATION APPARATUS WITH SELECTORS FOR SELECTING A PATIENT CATEGORY AND COMPATIBLE VENTILATION MODES

(71) Applicant: Air Liquide Medical Systems, Antony (FR)

(72) Inventors: Leslie Russo, Sivry-Courtry (FR); Maxime Derache, Massy (FR)

(73) Assignee: Air Liquide Medical Systems, Antony (FR)

( * ) Notice: Subject to any disclaimer, the term of this patent is extended or adjusted under 35 U.S.C. 154(b) by 364 days.

(21) Appl. No.: 16/598,770

(22) Filed: Oct. 10, 2019

(65) Prior Publication Data
US 2020/0114102 A1    Apr. 16, 2020

(30) Foreign Application Priority Data

Oct. 12, 2018   (FR) ...................... 1859472

(51) Int. Cl.
    *A61M 16/00*   (2006.01)
(52) U.S. Cl.
    CPC ...... *A61M 16/024* (2017.08); *A61M 16/0066* (2013.01); *A61M 2205/502* (2013.01); *A61M 2205/52* (2013.01); *A61M 2205/583* (2013.01); *A61M 2205/587* (2013.01); *A61M 2240/00* (2013.01); *A61M 2250/00* (2013.01)
(58) Field of Classification Search
    CPC ............. A61M 16/00; A61M 16/0057; A61M 16/0066; A61M 16/0069; A61M 16/021; A61M 16/022; A61M 16/024; A61M 2205/50; A61M 2205/502; A61M 2205/505; A61M 2205/52; A61M 2205/583; A61M 2205/587
    See application file for complete search history.

(56) References Cited

U.S. PATENT DOCUMENTS 5,752,509 A  *  5/1998  Lachmann .......... A61M 16/024
                                           128/203.12
6,099,481 A     8/2000  Daniels et al.
                (Continued)

FOREIGN PATENT DOCUMENTS

FR        3 051 117      11/2017
WO     WO 98 41270       2/1998

OTHER PUBLICATIONS

French Search Report for corresponding FR 1859472, dated May 29, 2019.

*Primary Examiner* — Joseph D. Boecker
(74) *Attorney, Agent, or Firm* — Allen E. White

(57) ABSTRACT

The invention relates to a medical ventilation apparatus (1) having a micro-blower (2) connected fluidically to a gas circuit (3) in order to supply said gas circuit (3) with respiratory gas, a controller (4) controlling the micro-blower (2), an electronic memory (8) configured to store at least several ventilation modes (Modes 1-6), and one or more patient category selectors (6) making it possible to select at least one given patient category from several selectable patient categories (6), and one or more ventilation mode selectors (7) making it possible to select at least one ventilation mode from among several selectable ventilation modes (Modes 1-6) based on the given patient category selected by means of said at least one patient category selector (6).

15 Claims, 2 Drawing Sheets

(56) References Cited

U.S. PATENT DOCUMENTS

| | | | | |
|---|---|---|---|---|
| 2001/0027791 A1* | 10/2001 | Wallace | ............ | A61M 16/024 128/204.21 |
| 2003/0062045 A1* | 4/2003 | Woodring | ......... | A61M 16/024 128/204.18 |
| 2008/0072902 A1 | 3/2008 | Setzer et al. | | |
| 2010/0229867 A1* | 9/2010 | Bertinetti | ............ | A61M 16/16 128/205.25 |
| 2011/0138315 A1* | 6/2011 | Vandine | ........... | A61M 16/0051 715/780 |
| 2012/0060840 A1* | 3/2012 | Refsland | .......... | A61M 16/0051 128/204.23 |
| 2013/0032147 A1* | 2/2013 | Robinson | ........... | A61M 16/021 128/204.18 |
| 2016/0228671 A1* | 8/2016 | Jackson | ............. | A61M 16/024 |
| 2016/0256642 A1* | 9/2016 | Soysa | ................... | A61M 16/16 |
| 2019/0143059 A1* | 5/2019 | Sanborn | ............. | A61M 16/024 128/202.22 |

\* cited by examiner

[Fig.1]
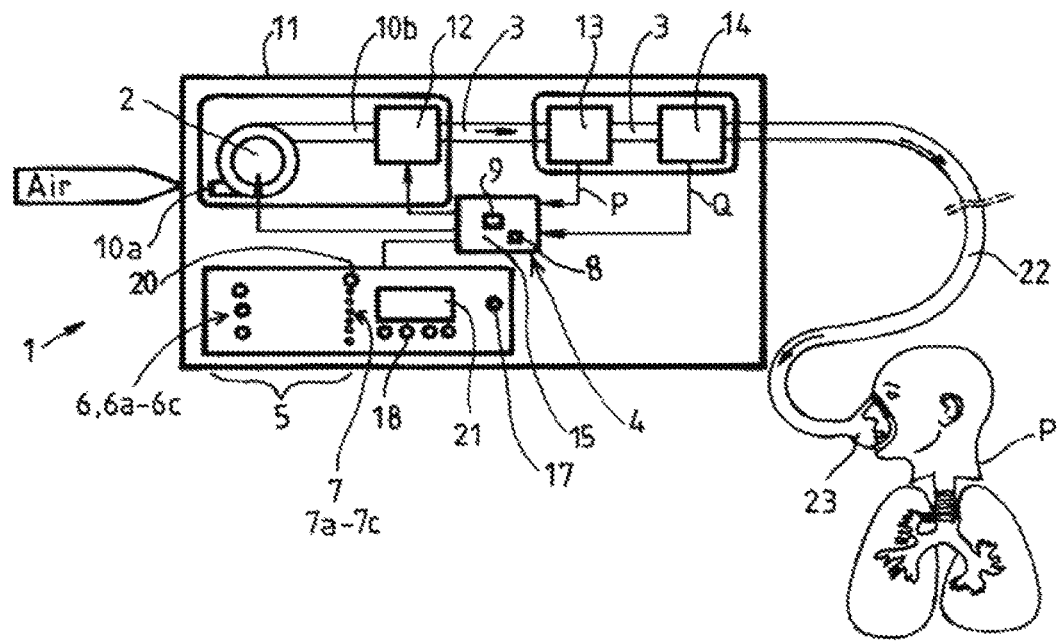
[Fig.2]
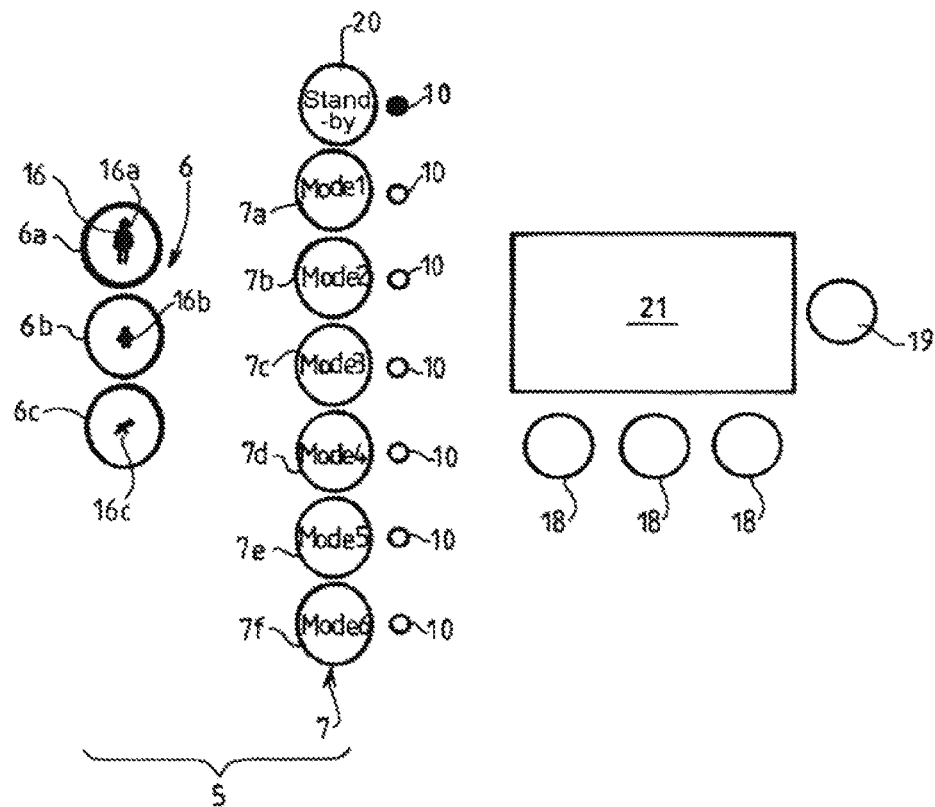

[Fig.3]
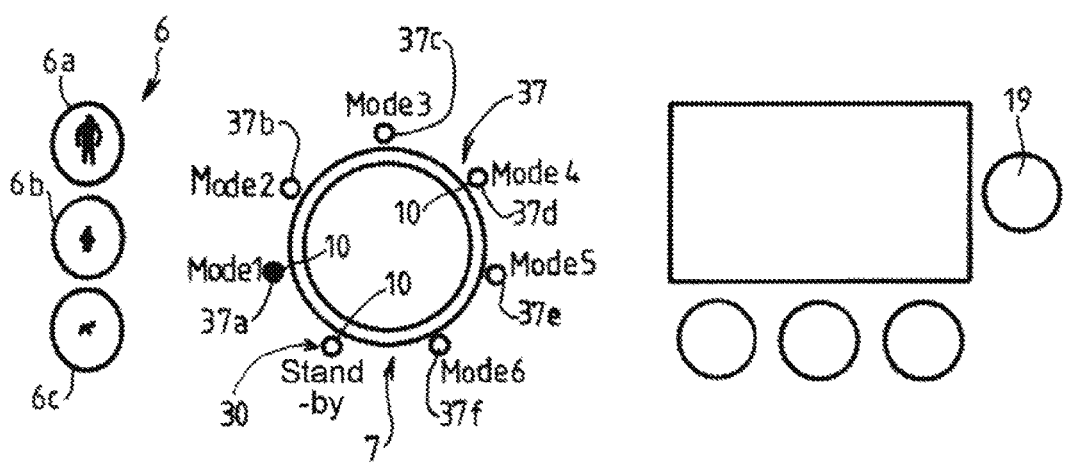
[Fig.4]
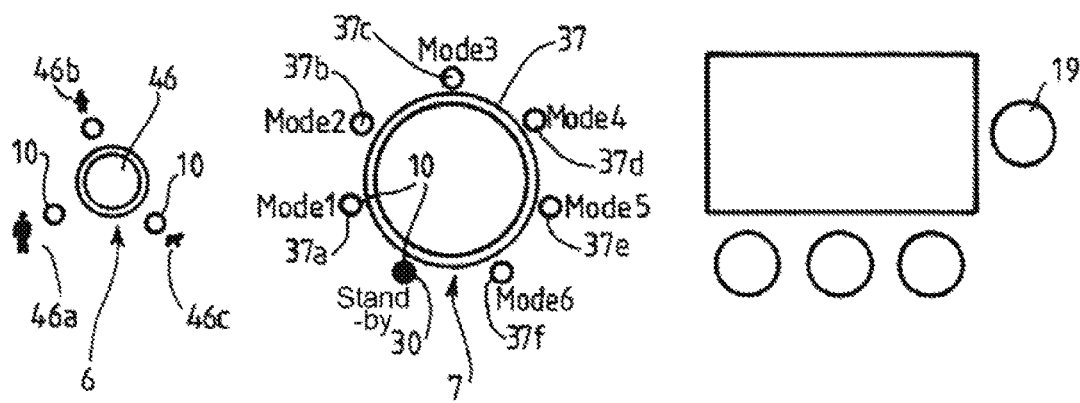

MEDICAL VENTILATION APPARATUS WITH SELECTORS FOR SELECTING A PATIENT CATEGORY AND COMPATIBLE VENTILATION MODES

CROSS REFERENCE TO RELATED APPLICATIONS

This application claims the benefit of priority under 35 U.S.C. § 119 (a) and (b) to French Patent Application No. 1859472, filed Oct. 12, 2018, the entire contents of which are incorporated herein by reference.

BACKGROUND

The invention relates to artificial ventilation apparatuses or devices comprising simple and intuitive means for selection of the ventilation parameters, namely the ventilation mode and the category of patient to be ventilated, making it possible to enhance the safety of ventilation by avoiding the choice of ventilation parameters that are incompatible with one another.

The artificial ventilation devices or apparatuses, also called respiratory assistance apparatuses, or more simply medical ventilators, are used to deliver a respiratory gas, such as air or oxygen-enriched air, to patients suffering from various respiratory diseases or disorders, for example sleep apnoea. The patients may be adults or children, even infants, that is to say babies.

In general, a medical ventilator provides different ventilation modes from which the user, i.e. the healthcare provider, is able to select according to the pathology presented by the patient who is to be treated, for example a ventilation mode dedicated to cardiopulmonary resuscitation, called the "CPV mode", for a patient in cardiac arrest, or a continuous positive airway pressure mode, or "CPAP mode", for a patient suffering from sleep apnoea.

The user can then parametrize the chosen ventilation mode, for example by setting the desired pressure level(s), the desired oxygen content ($FiO_2$), or can select default parameters (pre)recorded in a memory of the ventilator. In fact, an artificial ventilation device generally provides a plurality of default settings for each mode and for each type of patient, namely adult, child or infant, i.e. baby or neonate.

The choice of the ventilation mode and of the type or category of patient to be ventilated is made by means of a setting system integrated in the device.

Now, a given ventilation mode provided by a respiratory assistance apparatus is not necessarily usable for all categories, i.e. the types of possible patients.

For example, depending on the specifications of the apparatus, it can happen that the "CPV" mode is usable only on adult patients, on account of the fact that it integrates, for example, sensors that are not appropriate for children or infants, meaning that it is impossible to ensure an effective CPV mode on non-adult patients.

A user must not therefore be able to make a mistake by selecting a ventilation mode not compatible with a given patient category which is non-compatible with the selected mode.

However, this is often not taken into account in the existing apparatuses and thus poses serious problems for the patients as regards the safety of ventilation and the efficacy of treatment and can lead to barotrauma or to inappropriate ventilation that is wholly or partially ineffective, for example hypoventilation. There is also a risk of incorrect monitoring, which can lead to diagnostic errors and therefore to setting errors, which themselves can trigger excessive gas insufflation, thereby leading to a risk of barotrauma.

Moreover, during the powering up of the ventilator, that is to say during its start-up, it is imperative that the ventilation does not commence before the user has explicitly selected the ventilation mode adapted to the pathology presented by the patient who is to be treated.

The problem is therefore to make available an improved artificial ventilation device or apparatus with which, after powering up the apparatus, it is possible to make a simple and intuitive selection of the ventilation parameters, namely the ventilation mode and the category (or type) of patient who is to be ventilated, but without its being possible to select a ventilation mode not adapted to a given patient, and to then initiate a ventilation based on the selected parameters, preferably in at most two operations, so as to enhance patient safety and to ensure improved efficacy of treatment.

SUMMARY

The solution proposed by the invention thus concerns an artificial ventilation apparatus, that is to say a medical ventilator adapted to the ventilation of patients, comprising:
  a micro-blower, also called a compressor or turbine, connected fluidically to a gas circuit for supplying said gas circuit with respiratory gas, such as air or oxygen-enriched air,
  control means controlling the micro-blower,
  storage means configured to store at least several ventilation modes, and
  selection means actuatable by a user, typically a healthcare provider (e.g. physician, nurse, etc.) in order to allow said user to select a desired patient category and a ventilation mode,
characterized in that the selection means comprise:
  one or more patient category selectors for selecting at least one given patient category from several selectable patient categories, and
  one or more ventilation mode selectors for selecting at least one ventilation mode from several selectable ventilation modes depending on the given patient category selected by means of said at least one patient category selector, and in which the one or more ventilation mode selectors are configured such that at least one ventilation mode is not selectable in combination with at least one patient category selected by the one or more patient category selectors.

In other words, according to the invention, the ventilation mode selector(s) and/or the patient category selector(s) cooperate together and are especially adapted and/or designed for it to be impossible to select a ventilation mode not adapted to a given patient category.

Once the patient category selector has been activated by the user by placing a finger or hand on the one or more category selectors, only the ventilation modes adapted to the chosen patient category can be selected by means of the ventilation mode selector(s). Some mode/category combinations are thus rendered impossible or thwarted, so as to enhance patient safety by avoiding the possibility of choosing an incorrect mode.

Depending on the circumstances, the ventilation apparatus of the invention can comprise one or more of the following technical features:
  the patient category selector(s) and the ventilation mode selector(s) are chosen from rotary selector knobs and selection buttons, the patient category selectors preferably comprise several selection buttons, the patient category selectors comprise several selection buttons actuatable by digital actuation by a user, that is to say typically by pressure of the finger, for example the index finger, the patient category selectors comprise 2 to 10 selection buttons, preferably 3 to 5 buttons, the patient category selectors comprise three selection buttons configured to permit selection of a given patient category chosen from the (patient) categories: adult, child and infant, the patient category selection buttons are each indicated by a pictogram (i.e. a graphical representation) representing a given patient category, the three patient category selection buttons are indicated respectively by a first pictogram representing an adult, a second pictogram representing a child, and a third pictogram representing a neonate, the ventilation mode selectors comprise several selection buttons actuatable by digital actuation by a user, that is to say typically by pressure of the finger, for example the index finger, the ventilation mode selectors comprise at least three selection buttons that are configured in each case to permit selection of a given ventilation mode from several ventilation modes recorded in the storage means, typically between 4 and 10 selection buttons, preferably between 5 and 8 selection buttons, it additionally comprises a stand-by button corresponding to a stand-by mode in which no ventilation mode is selected. When the apparatus is in stand-by, the control means do not order delivery of gas by the micro-blower, that is to say the ventilation by delivery of gas does not take place when this stand-by button is activated by the user.

the ventilation mode selection buttons and/or the stand-by button are each indicated by a luminous indicator, preferably diodes of the LED type or similar, the luminous indicators are arranged alongside, that is to say opposite and close to, the ventilation mode selection buttons and/or the stand-by button, the luminous indicators are carried by the shell of the ventilator, for example are fastened through the wall of the shell, the patient category selection buttons are arranged in a first line or in a row, i.e. are aligned, the ventilation mode selection buttons are arranged in a second line or in a row, i.e. are aligned, the first line or row and the second line or row may or may not be parallel, the ventilation mode selection buttons are identical to or different from one another, preferably identical or similar buttons, in particular in terms of dimensions and shapes, the patient category selection buttons are identical to or different from one another, preferably identical or similar buttons, in particular in terms of dimensions and shapes, the patient category selection buttons and or the ventilation mode selection buttons are back-lit, the control means controlling the micro-blower comprise at least one microprocessor, in particular at least one microcontroller, the control means controlling the micro-blower comprise at least one electronic board comprising said at least one microprocessor, the control means controlling the micro-blower comprise at least one microprocessor using one or more algorithms, the storage means comprise one or more memories, the storage means comprise one or more random access memories (RAM) serving especially to provisionally or temporarily store parameters, data, information, etc. Generally, a RAM permits more rapid recording, but the latter is erased when the apparatus is switched off.

the storage means comprise one or more flash memories serving to record parameters, data, information, etc., and preserve them permanently in the apparatus, especially modifications of the parameters of the different ventilation modes actuated by the user, the flash memory is preferably a persistent memory which preserves the recorded data after the apparatus has been stopped, the storage means are configured to safeguard or not to safeguard the user settings upon voluntary switching off of the apparatus, at least one memory is carried by the electronic board comprising the one or more microprocessors of the control means, the storage means are configured to record (i.e. store) the ventilation modes associated with one or more patient categories, the storage means are configured to record (i.e. store) the parameters of the different ventilation modes, the control means cooperate with the storage means to retrieve the one ore more stored ventilation modes corresponding to the patient category having been selected by means of the one or more patient category selectors, in particular the patient category selection buttons, that is to say to retrieve the one ore more ventilation modes stored in association with a given patient category, the control means cooperate with the one or more ventilation mode selectors, in particular the ventilation mode selection buttons, to authorize the selection of at least one ventilation mode by actuation, by the user, of one or more ventilation mode selectors, in particular one or more ventilation mode selection buttons. This makes it possible to authorize a selection, by the user, of all the ventilation modes adapted to a selected patient category, for example to authorize the selection of all the ventilation modes for an adult patient.

the control means cooperate with the one or more ventilation mode selectors, in particular the ventilation mode selection buttons, to prohibit or thwart the selection of at least one ventilation mode by actuation, by the user, of one or more ventilation mode selectors, in particular one or more ventilation mode selection buttons. This makes it possible to prevent a selection, by the user, of a ventilation mode not adapted to the selected patient category, for example to prevent adopting the CPV mode for an infant.

the control means control at least the micro-blower depending on the patient category and the associated ventilation mode that have been selected by means of the one or more patient category selectors and of the one or more ventilation mode selectors.

the storage means are configured to store several ventilation modes chosen from the modes CPV (cardiopulmonary ventilation for cardiac resuscitation), PACV (pressure assist-control ventilation, with an inhalation trigger, for a patient having sufficient strength to trigger a respiratory cycle. The activation/deactivation of the trigger is one of the parameters that can be modified by the user), ASB (assisted spontaneous breathing, used for example in the context of weaning the patient or in the management of decompensation in a patient with COPD (chronic obstructive pulmonary disease), CPAP (continuous positive airway pressure) and HFOT (high-flow oxygen therapy).

the storage means are configured to store a stand-by mode in which no ventilation mode is selected and/or in which no ventilation is delivered, i.e. performed, by the apparatus.

each ventilation mode comprises ventilation parameters comprising one or more values for gas pressure, gas flowrate and respiratory frequency, and possibly $FiO_2$. The ventilation parameters depend on the ventilation mode selected by the user, for example:
  in the CPV mode, the user can set the $FiO_2$ setpoint, the inhalation aid setpoint called high pressure or HP (i.e. a pressure value), the respiratory frequency setpoint and the PEP or positive end pressure setpoint, also called low pressure or LP (with LP<HP).
  in the HFOT mode, the user can set the $FiO_2$ setpoint and the flowrate setpoint,
  in the PACV mode, the user can set the $FiO_2$ setpoint, the inhalation aid setpoint, the respiratory frequency setpoint, the PEP setpoint and the deactivation/activation of the inhalation trigger.
  in the ASB mode, the user can set the $FiO_2$ setpoint, the inhalation aid setpoint and the PEP setpoint.
  and in the CPAP mode, the user can set the $FiO_2$ setpoint and the CPAP setpoint (pressure value).

the storage means control at least the micro-blower according to one or more ventilation parameters of the selected ventilation mode corresponding to the chosen patient category.

according to another embodiment, the patient category selector and the ventilation mode selector comprise rotary selector knobs, also called rotary switches.

a first rotary selector knob makes it possible to choose the patient category.

a second rotary selector knob makes it possible to choose a ventilation mode corresponding to the selected patient category.

the rotary selector knobs are manoeuvrable in rotation by the user, in the direction of the hands of a clock and/or in the opposite direction the manoeuvrable rotary selector knobs are movable in rotation between several predefined positions corresponding to different ventilation modes, that is to say each position corresponding to a given ventilation mode for which the settings (i.e. setpoint values, etc.) are predefined and recorded.

the second rotary selector knob is manoeuvrable between several predefined positions corresponding to ventilation modes and a stand-by mode corresponding to a "stand-by" mode in which the ventilation by delivery of gas does not take place, that is to say no gas is delivered by the micro-blower.

the rotary selector knobs are movable in rotation between several positions angularly offset from one another, that is to say offset in an arc of a circle.

the luminous indicators are arranged around the rotary selector knobs in line with the angularly offset positions, in particular in an arc of a circle.

the names of the modes and the names or graphical representations of the patient categories can be screen-printed or affixed (e.g. glued) to the shell of the apparatus in line with the rotary selector knobs.

according to another embodiment, also called a "mixed" embodiment, the patient category selectors comprise several selection buttons (as in the first embodiment described above), while the ventilation mode selector comprises a rotary selector knob (as in the second embodiment described above), or vice versa.

Generally, regardless of the embodiment chosen, the ventilation apparatus of the invention can also comprise one or more of the following technical features:
  the micro-blower delivers air, oxygen-enriched air or pure oxygen as respiratory gas, preferably air.
  the micro-blower comprises an electric motor.
  the micro-blower comprises an electric motor comprising a rotary axle or shaft carrying at least one bladed wheel.
  the micro-blower comprises an electric motor surmounted by a volute arranged around the bladed wheel, that is to say the volute defines an internal compartment in which the bladed wheel is arranged.
  the volute comprises a gas inlet and a gas outlet.
  the volute is surmounted by a cowl.
  the motor is designed to be able to reach a rotation speed of up to at least 40,000 revolutions per minute (rpm), preferably up to about 70,000 rpm.
  the micro-blower is controlled by the control means.
  the motor is of the brushless type.
  the motor is of the type with low inertia.
  it comprises means for supplying electric current, such as a rechargeable battery and/or a cord with plug for connection to the mains (i.e. 110/220 V).
  the means for supplying electric current supply electric current to the various components requiring electricity to function, in particular the electric motor of the micro-blower, the control means, especially the electronic board, the diodes or other lights of the apparatus, etc.
  it comprises an outer shell in which are arranged the micro-blower, all or part of the gas circuit, the control means controlling the micro-blower, typically an electronic board with microcontroller, and the storage means, in particular the flash memory and the RAM.
  the one or more patient category selectors and the one or more ventilation mode selectors are arranged (i.e. supported) on the outer shell of the apparatus.
  it comprises a pressure sensor and/or a flowrate sensor which are arranged in such a way as to measure the pressure and/or the flowrate of the gas in the gas circuit, downstream from the micro-blower.
  it comprises at least one actuator arranged downstream from the micro-blower in order to control the gas flowrate in the gas circuit, in particular one or more solenoid valves.
  the control means are configured to:
  I) retrieve, from the ventilation modes stored by the storage means, at least one given ventilation mode in response to a selection, by the user, of a patient category and said ventilation mode by actuation of one of the patient category selection buttons and one of the ventilation mode selection buttons,
  ii) control at least the micro-blower in such a way that it delivers respiratory gas according to the selected ventilation mode.
  the control means are configured to control at least the micro-blower and at least one actuator, especially one or more solenoid valves.

- the apparatus comprises a graphical user interface or GUI and/or or a human machine interface or HMI.
- the GUI or HMI comprises setting means (e.g. keys, buttons, cursors or others) and a graphical display, that is to say a graphical display screen, for example a touch screen, preferably with virtual buttons.
- the apparatus is configured such that a given patient category, for example the adult category, is selected by default, in particular when starting up the apparatus. In this case, one action of the user suffices to select a compatible ventilation mode in order to start up the ventilation in adult category.
- the apparatus also comprises a validation button with which it is possible to confirm the selection of a ventilation mode by means of the one or more ventilation mode selectors.
- the apparatus is configured such that it is by default in the adult patient category and in stand-by mode at the time it is started up, i.e. switched on.
- according to one embodiment, the apparatus is configured in such a way that going from the stand-by mode to a ventilation mode, with (preferably immediate) initiation of the ventilation by control of the micro-blower, requires successively the activation, by the user, of at least:
  a) the one or more ventilation mode selectors for selecting a given ventilation mode compatible with the selected patient category, and
  b) the validation button for confirming the selection of the selected ventilation mode.
- according to another embodiment, the apparatus is configured in such a way that going from the stand-by mode to a ventilation mode, with (preferably immediate) initiation of the ventilation by control of the micro-blower, requires only one activation, by the user, of the one or more ventilation mode selectors for selecting a given ventilation mode compatible with the selected patient category, that is to say without validation by actuation of the validation button.
- the apparatus is moreover configured in such a way that going from the stand-by mode to a ventilation mode requires, prior to the selection of a given ventilation mode, an activation, by the user, of the one or more patient category selectors in order to select a desired patient category, this irrespective of the embodiment in question.
- according to another embodiment, the apparatus is moreover configured in such a way that going from the stand-by mode to a ventilation mode requires only one selection of a given ventilation mode, when a patient category is selected by default at the start-up of the apparatus or has already been selected beforehand. In this case, the user does not have to select the patient category by actuation of the one or more patient category selectors, since the patient to be treated corresponds to the default patient category or the patient category already selected during a preceding ventilation.
- the apparatus is additionally configured in such a way that, during a ventilation, that is to say after initiation of the ventilation of a patient, two successive actions are required in order to modify the ventilation mode, namely first of all the choice of a new ventilation mode compatible with the selected patient category, followed by a validation of this new ventilation mode by activation/actuation of the validation button. This makes it possible to avoid any untimely or inadvertent change of ventilation mode.
- it is configured such that, during a ventilation, modifying the ventilation mode requires successively the activation, by the user, of:
  a) the one or more ventilation mode selectors for passing from a first ventilation mode to a desired second ventilation mode compatible with the selected patient category, and
  b) the validation button for confirming the selection of said selected second ventilation mode.
- in particular, the move to or the selection of the HFOT mode (high-flow oxygen therapy) always requires an activation, by the user, of the validation button in order to confirm the section of the HFOT mode. This is because the HFOT mode is a mode that requires a specific respiratory interface, and therefore it must not be possible to initiate it without the need for confirmation after its selection.

BRIEF DESCRIPTION OF THE DRAWINGS

The invention will now be better understood from the following detailed description given as a non-limiting example and with reference to the appended figures, in which:

FIG. 1 shows a schematic view of a first embodiment of an artificial ventilation apparatus according to the present invention, FIG. 2 shows a schematic view of a first embodiment of an artificial ventilation apparatus according to the present invention, FIG. 3 shows a schematic view of other embodiments of an artificial ventilation apparatus according to the present invention.

FIG. 4 shows a schematic view of other embodiments of an artificial ventilation apparatus according to the present invention.

DETAILED DESCRIPTION OF PREFERRED EMBODIMENTS

FIG. 1 is a schematic view of an embodiment of a ventilation apparatus 1 or medical ventilator according to the present invention, and FIG. 2 is a schematic view of a first embodiment of the patient category 6 selection means 5 and ventilation mode selection means 7 according to the invention, which are incorporated in the apparatus of FIG. 1.

This ventilation apparatus 1 comprises an outer shell 11, for example of polymer, in which the various components of the apparatus 1 are arranged. More precisely, this apparatus 1 comprises a micro-blower 2, also called a turbine or compressor, which draws in ambient air via an air inlet 10a and which is moreover fluidically connected, downstream/at outlet 10b, to a gas circuit 3 comprising an internal passage or conduit for gas, so as to supply the gas circuit 3 with respiratory gas delivered by the micro-blower 2.

Typically, the respiratory gas is air, or oxygen-enriched air or pure oxygen, especially depending on the therapy/ventilation to be implemented.

The internal gas circuit 3 of the apparatus 1 is fluidically connected to the patient P via a flexible conduit 22 and a respiratory interface 23 such as a breathing mask, a tracheal tube or similar, so as to supply the patient P with respiratory gas.

The micro-blower 2 is motorized, that is to say it has an electric motor, typically a brushless motor with a rotation speed of up to 40,000 rpm, or even 70,000 rpm, and preferably also having a low inertia. Classically, such a micro-blower 2 comprises an electric motor which is protected by a casing and, during its operation, drives an axle or rotary shaft carrying a bladed wheel arranged in the internal compartment of a volute which surmounts the electric motor and the casing. The volute comprises a gas inlet through which the air aspirated via the inlet 10*a* enters the internal compartment, and a gas outlet via which the pressurized gas leaves the internal compartment and then travels from the outlet 10*b* into the conduit 3. The volute can be surmounted by a cowl.

In order to control the passage of gas in the circuit 3, that is to say in the direction of the patient P, one or more actuators 12 are provided, for example one or more solenoid valves arranged on the pathway of the gas (e.g. on the internal circuit), downstream from the micro-blower 2, and one or more pressure sensors 13 (P) and or flowrate sensors 14 (Q) are also arranged on the pathway of the gas, that is to say in such a way as to perform measurements in the gas circuit 3, in particular downstream from the one or more actuators 12.

Control means 4 are also provided for controlling the one or more actuators 12 and also the micro-blower 2 according to settings stored in the form of ventilation modes, as is explained below.

The control means 4 advantageously comprise one or more microprocessors 9, preferably one or more microcontrollers. Typically, the microprocessor 9 is carried by an electronic board 15. The microprocessor 9 uses one or more algorithms.

The micro-blower 2, the one or more actuators 12 and the one or more sensors 13, 14 are also connected electrically to the control means 4, in particular to the processor carried by the electronic board of said control means 4. Indeed, the micro-blower 2 is controlled by the control means 4, for example via a direct-voltage value generated with the aid of an all-or-nothing signal, typically a control by pulse-width modulation (PWM), or a current value, and is regulated by pressure monitoring, in particular via the pressure data (P) measured by the pressure sensor 13.

Thus, the one or more pressure and/or flowrate sensors 13, 14 make it possible to transmit pressure data (P) and/or flowrate data (Q) to the control means 4, and the latter are able to act on the one or more actuators 12, in particular in order to adjust, stop or regulate the supply of gas originating from the micro-blower 2. In other words, the control means 4 recover the signals originating in particular from the sensors 13, 14, process/analyze them, and then control in particular the one or more actuators 12 and/or the micro-blower 2 in accordance with this processing.

Moreover, storage means 8 are also provided, such as one or more memories for recording of data, which storage means 8 can also be carried by the electronic board 15. They are in particular configured to store several ventilation modes and combinations of patient category/ventilation mode.

Advantageously, the apparatus 1 comprises, as storage means 8, a flash memory serving as a read-only memory and moreover a random access memory (RAM).

The flash memory makes it possible to record and preserve the parametrization of the ventilation modes, that is to say the pressure values, flowrate, etc. associated with each ventilation mode, and also the default values, the combinations of ventilation/patient category modes and other data, information items, operating parameters or other parameters to be retained in the apparatus 1. The stored ventilation modes are, for example, a CPV mode, a CPAP mode, PACV, ASB, HFOT or any other ventilation mode.

Moreover, the RAM memory makes it possible to temporarily store any parameter modifications that are desired by the user, or any other data, information items or provisional parameters. These modifications can be entered in the apparatus 1 by means, for example, of a graphical user interface (GUI) or a human machine interface (HMI) comprising setting means 18 (e.g. keys, buttons, cursors or others) and a graphical display screen 21 in colour or in black and white. The graphical display screen 21 can be a touch screen, and the setting means 18 of the GUI or of the HMI serving to modify or adjust the ventilation settings (i.e. parameters) are then preferably virtual or analog buttons showing on said touch screen.

The control means 4, in particular the microprocessor 9, cooperate with the storage means 8, i.e. flash memory and RAM, in order to recover from them useful information items, parameters or other data, in particular the authorized or possible ventilation mode/patient category mode combinations, as explained below.

The apparatus 1 moreover comprises selection means 5, for example arranged on one of the outer walls or faces of the shell 11, for example on the front, which selection means 5 can be operated by digital or manual pressure applied by a user, that is to say a healthcare provider such as a physician, a nurse or similar, in order to allow said user to select a given ventilation mode from those stored, i.e. recorded, by the storage means 5, in accordance with a desired patient category.

To do this, the user first of all selects the patient category corresponding to the patient P who is to be treated by administration of respiratory gas, as is explained below. The patient categories that can be selected are preferably adults, children and infants (i.e. babies, neonates, etc.), whether male or female.

In general, a category is understood as follows:
adult: for persons (i.e. about >18 years) having a pulmonary volume of the order of 200 ml to 1000 ml,
child: for young persons (i.e. about <18 years) having a pulmonary volume of the order of 50 to 300 ml, that is to say a minimum weight of 8 kg,
infant: for very young persons having a pulmonary volume of the order of 20 to 70 ml, that is to say a weight of less than about 8 kg.

The volumes indicated are linked to the weight of the patient rather than to his or her age and/or height.

According to the invention, in the embodiment of FIGS. 1 and 2, the selection means 5 comprise several patient category selectors 6, namely three buttons 6*a*-6*c*, each corresponding to a given patient category, that is to say adult, child or infant, and several ventilation mode selectors 7, namely six buttons 7*a*-7*f* also allowing a given ventilation mode to be selected from one or more possible ventilation modes, for example CPV, CPAP, etc., depending on the given patient category selected by means of the patient category selectors 6.

The one or more ventilation modes inappropriate, i.e. prohibited, with respect to a given patient category cannot be selected by means of the ventilation mode selectors 7, since such selections are thwarted or made impossible by the control means 4. For example, in the case of buttons, the user can still press on a button corresponding to an inappropriate ventilation mode, but the algorithm (i.e the software) of the apparatus will not apply the new ventilation mode because it is incompatible with the chosen patient category. The selection indicator will therefore not be illuminated.

In other words, the ventilation mode selectors 7 make it possible to select only the one or more ventilation modes that are appropriate to the treatment of the patient category 6 having been chosen by actuation of one of the patient category selectors 6a-6c. This avoids selection of a ventilation mode that is incompatible with the category of patient to be treated, when the latter is not compatible with this ventilation mode.

For example, by virtue of the present invention, the healthcare provider would not be able to select the CPV mode to treat a neonate, even if the latter has suffered cardiac arrest, since the CPV mode is a ventilation mode dedicated to adults or certain children (i.e. adolescents, for example) and not at all suitable for infants, hence potentially dangerous for them, on account in particular of the ventilation volumes and/or pressures used, but also on account of the incorrect monitoring mentioned above.

More precisely, the various ventilation modes compatible with a given patient category, that is to say their ventilation parameters, are stored in the flash memory of the electronic board forming part of the storage means 8; they are preferably stored in combination with one or more possible, i.e. authorized, patient categories. The control means 4, in particular the microprocessor 9 and its algorithms (i.e. software), will then recover and propose to the user the one or more possible ventilation modes that have been stored in combination with the patient category selected by activation of a selection button of a patient category, thereby authorizing selection by the user of one or more ventilation mode selection buttons 7a-7f and possibly prohibiting the selection of one or more other buttons 7a-7f.

In other words, if a ventilation mode is selected by the user actuating ventilation mode selection buttons 7a-7f and this mode is not compatible with the chosen patient category, then the software will not apply the ventilation parameters corresponding to this "prohibited" mode. In this case, the mode selection indicator 10 will remain in the preceding mode or in stand-by P.

The solution afforded by the invention increases patient safety by avoiding a situation where personnel can make a mistake when opting for a ventilation mode, thus preventing, excluding or inactivating certain combinations of ventilation mode and patient category mode that are undesirable, that is to say incompatible, since they are likely to jeopardize the safety of the patient or may lead to a treatment that is ineffective on account of the ventilation parameters being inappropriate or poorly adapted.

In the embodiment of FIGS. 1 and 2, the patient category selectors 6 and ventilation mode selectors 7 comprise buttons 6a-6c, 7a-7f which are to be operated by a finger, that is to say by the user applying digital pressure, and which are arranged in two parallel rows of buttons 6, 6a-6c; 7, 7a-7f carried by one of the walls of the shell 11 of the apparatus 1. A different arrangement is of course possible.

As is shown schematically in FIG. 1, each patient category selection button 6a-6c bears a pictogram 16 representing a given patient category, in this case three buttons 6a-6c bearing pictograms 16 representing an adult 16a, a child 16b and an infant 16c, respectively. Advantageously, the patient category selection system 6 has as many selection buttons 6a-6c as there are types of patients who are to be supported by the apparatus 1, that is to say who can be treated, that is to say it is possible to provide fewer than three buttons or more than three buttons, depending on the desired embodiment.

More precisely, the setting system, that is to say the selection means 5 activatable by the user in order to permit selection of a combination of ventilation mode and patient category, is connected to the processor present on the electronic board of the control means 4.

When the user presses on one of the patient category selection buttons 6a-6c, the button will then be lit or back-lit by lighting means, for example one or more diodes of the LED type, which activate when the user presses on the button concerned. For example, the lighting means can be arranged under the buttons 6a-6c, and the latter can be made of translucent material so as to be lit up from behind when they are activated.

Moreover, the ventilation mode selectors 7 comprise several selection buttons 7a-7f, preferably between 5 and 10 selection buttons, here for example 6 buttons, which are configured to permit in each case the selection of a given ventilation mode from several ventilation modes, called Modes 1 to 6, which are recorded in the storage means 8 in combination with one or more patient categories.

Here too, lighting means can be arranged under the buttons 7a-7f, and the latter can be made of a translucent material so as to be lit up from behind when they are activated.

The ventilation mode selection buttons 7a-7f are each indicated by a luminous indicator 10, preferably a diode of the LED type or similar, for example a diode of colour red, green, blue, orange, white yellow, etc. Each indicator 10 is arranged opposite one of the ventilation mode selection buttons 7a-7f in such a way as to indicate, when it lights, the button 7a-7f that is active. This allows the user to see immediately which ventilation mode is selected for the chosen patient category.

Of course, according to another embodiment, luminous indicators could also be provided to indicate the three patient category selection buttons 6a-6c. However, simple backlighting of the active button 6a-6c appears to be sufficient in practice.

Advantageously, the apparatus 1 also comprises a validation button 19 with which it is possible to confirm the selection of a ventilation mode by means of the one or more ventilation mode selectors 7a-7f. More precisely, the apparatus 1 is configured such that during a ventilation, that is to say after the ventilation of a patient has started, two successive actions are required to modify the ventilation mode, namely to move from one ventilation mode to another ventilation mode, so as to minimize the risk of error or of incorrect manipulation. Thus, it is first necessary to choose a new ventilation mode compatible with the patient category already selected, by activating one of the ventilation mode selection buttons 7a-7f in order to select a new ventilation mode different from the mode previously chosen, then to validate this new ventilation mode by activation/actuation of the validation button 19.

Moreover, the apparatus 1 can also be configured such that the activation of the validation button 19 is obligatory in order to confirm the selection of a particular ventilation mode, in particular of what is called a "risk" mode, typically at the change from the stand-by mode to this particular ventilation mode, for example the HFOT mode which requires the use of a specific respiratory interface for delivering the gas.

Preferably, the apparatus 1 is configured such that a given patient category, for example the adult category, is selected by default, in particular when starting up the apparatus 1. To put it another way, when the apparatus 1 is being started up, the button 6a is selected by default and is back-lit in order to show the user that this choice of adult category is made by default.

In this case, the user can then:
- either immediately choose a ventilation mode by pressing one of the ventilation mode buttons 7a-7f authorized for adult patients. One action of the user then suffices to select a compatible ventilation mode and to start up the ventilation in adult category.
- or first of all choose another patient category, that is to say child or infant, by pressing one of the patient category selection buttons 6b, 6c, then select a compatible ventilation mode by pressing on one of the ventilation mode buttons 7a-7f authorized for the chosen patient category, and finally validate this choice by acting on the validation button 19, as has been explained above.

It should be noted that when the apparatus 1 is started up, that is to say when the adult category button 6a is selected by default, no ventilation mode is selected by default, but the apparatus 1 is on stand-by, that is to say a stand-by button 20 is activated by default.

Indeed, as is illustrated in FIG. 2, a stand-by button 20 is also provided corresponding to a stand-by mode in which no ventilation mode is selected. This stand-by button 20 can also be indicated by a luminous indicator 10 such as a diode of the LED type or similar.

The lighting and the extinguishing of the luminous indicators 10 are also controlled by the control means 4.

In stand-by, the control means 4 do not order delivery of gas by the micro-blower 2, that is to say the ventilation by delivery of gas does not take place when this stand-by button is activated by the user. The stand-by button 20 can also be activated by the user in order to stop the ventilation by deselecting any ventilation mode. Preferably, any discontinuation of the ventilation by activation of (i.e. pressure on) the stand-by button requires a confirmation/validation of the user via the validation button 19 in order to avoid any untimely discontinuation of the ventilation of the patient.

Of course, the apparatus also comprises electrical supply means (not shown), in particular a rechargeable battery and/or a cord and plug for connection to the mains (e.g. 110/220V).

FIG. 3 shows a second embodiment, which is similar to the first embodiment of FIGS. 1 and 2, but in which the ventilation mode selection buttons have been replaced by a mechanical rotary selector 37, advantageously a rotary selector knob, moving between several positions 37a-37f, 30 offset at an angle to each other.

Each angular position 37a-37f corresponds to a given ventilation mode, called "Mode 1" to "Mode 6" respectively, as before, here for example 6 different ventilation modes. Of course, the number of modes can be greater or lesser than 6, typically between 4 and 15 modes, generally between 5 and 12 modes. An angular position 30 is also provided corresponding to a stand-by mode, ensuring the same function as the stand-by button 20 in FIGS. 1 and 2.

The different positions 37a-37f, 30 are arranged in a circle (an arc of a circle) around the knob 37 and are angularly offset from one another by an angle of the order of 51°, for example. Preferably, in order to assist the user in the choice of mode, the different positions can once again be indicated by a luminous indicator 10, such as an LED or similar. The different indicators are arranged, likewise in a circle (an arc of a circle), around the rotary knob 37 opposite the positions 37a-37f of "Modes 1 to 6" and the position of the stand-by 30.

During the operation of the apparatus 1, once the user has selected the patient category by pressing on one of the buttons 6a-6c as above, the selected button 6a-6c is back-lit and, furthermore, all or some of the different positions 37a-37f corresponding to ventilation Modes 1 to 6, which are available and compatible with the patient category selection made, also light up around the rotary selection knob 37, whereas those that are unavailable and/or incompatible remain unlit. This can once again result from the use of back-lighting produced by lighting means as described above. By default, the rotary knob 37 is in stand-by position 30.

The rotary knob 37 or mechanical selector can then be manoeuvred in rotation by the user. The rotation of the knob 17 causes the displacement of a selection marker, which moves from one luminous indicator 10 to another, that is to say from a position (37a-37f) to the following angularly offset position which is available, hence from a ventilation mode to the following mode, as above. The displacement of the selection marker thus takes place in the same direction of rotation as that of the rotary knob 37, that is to say clockwise or anticlockwise depending on the direction in which the user turns the knob 37.

The selection marker "skips" the modes that are not lit, thereby preventing any selection of a mode that is unavailable in the selected patient category.

Thereafter, the ventilator 1 applies to the ventilation the default settings or ventilation parameters that are stored and are adapted to the patient category and mode selected by the user, as has already been explained.

Preferably, the stand-by position 30 corresponds to a stand-by mode or pause mode in which the ventilation by delivery of gas is not carried out. By default, this is the mode that is automatically selected upon start up, i.e. initiation, of the apparatus 1, in the absence of any action by the user. A luminous indicator 10 (LED) will light automatically at the start up of the apparatus 1, in order to indicate to the user that the apparatus is in stand-by.

FIG. 4 shows a third embodiment, which is similar to the second embodiment of FIG. 3 and in which the ventilation mode is selected via a first mechanical rotary selector 37, for example a rotary selector knob, moving between several positions 37a-37f and a stand-by position 30 which are angularly offset from one another, as has already been explained, and in which the patient category buttons (adult, child infant) have also been replaced by a second mechanical rotary selector 46, advantageously a rotary selector knob 46, moving between several positions 46a-46c angularly offset from one another, namely three positions corresponding to the patient types adult, child and infant.

As in the embodiment of FIG. 3, the positions of the two rotary selector buttons 37, 46 are preferably indicated by luminous indicators 10, such as diodes that light up.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:
1. A ventilation apparatus (1) comprising:
a micro-blower (2) connected fluidically to a gas circuit (3) and configured to supply said gas circuit (3) with respiratory gas, a controller (4) configured and adapted to control operation of the micro-blower (2), an electronic memory (8) configured to store at least several ventilation modes (Modes 1-6), and a user interface (5) capable of being actuated by a user to thereby allow said user to select a desired ventilation mode and a desired patient category, characterized in that the user interface (5) comprises:

one or more patient category selectors (6) configured to enable said user to select the desired patient category from several user selectable patient categories (6), and one or more ventilation mode selectors (7) from among the several selectable ventilation modes (Modes 1-6) based on the desired patient category (6), and wherein the one or more ventilation mode selectors (7) are configured such that at least one ventilation mode (Modes 1-6) is not selectable in combination with at least one patient category (6).

2. The apparatus of claim 1, wherein the one or more patient category selectors (6) and the one or more ventilation mode selectors (7) are chosen from among rotary knobs and buttons.

3. The apparatus of claim 2, wherein the user interface (5) comprises several selection buttons (6a-6c; 7a-7f) that can be actuated by digital actuation (i.e. pressure of the finger) by said user.

4. The apparatus of claim 2, wherein the patient category selectors (6) comprise three selection buttons (6a-6c) configured to permit the selection of the desired patient category chosen from the categories adult, child and infant.

5. The apparatus of claim 2, wherein the ventilation mode selectors (7) comprise at least three selection buttons (7a-7f), each configured to permit the selection of the desired ventilation mode from among the several ventilation modes (Modes 1-6) registered in the electronic memory (8).

6. The apparatus of claim 5, further comprising a stand-by button (P) corresponding to a stand-by mode for which no ventilation mode is selected and/or no ventilation is performed.

7. The apparatus of claim 6, wherein the ventilation mode selection buttons (7a-7f) and/or the stand-by button (P) are each indicated by a luminous indicator (10).

8. The apparatus of claim 4, wherein the selection buttons (6a-6c) are each indicated by a pictogram (16) depicting one of the user selectable patient categories, in particular a pictogram (16) depicting an adult (16a), a child (16b) and an infant (16c).

9. The apparatus of claim 1, further comprising a validation button (19) for confirming the selection of one of the-a ventilation modes (Mode 1-6).

10. The apparatus of claim 1, wherein the controller (4) is configured and adapted to cooperate with the electronic memory (8) to be operable to retrieve the one or more stored ventilation modes (Modes 1-6) corresponding to the desired patient category that has been selected by means of the one or more patient category selectors (6).

11. The apparatus of claim 1, wherein the controller (4) is configured and adapted to cooperate with the one or more ventilation mode selectors (7) to:

a) authorize the selection of at least one ventilation mode (Modes 1-6) by the actuation, by the user, of one or more ventilation mode selectors (7), and/or b) prohibit the selection of at least one ventilation mode (Modes 1-6) by the actuation, by the user, of one or more ventilation mode selectors (7).

12. The apparatus of claim 1, wherein the controller (4) is configured to control at least the micro-blower (2) depending on the desired patient category and the associated desired ventilation mode that have been selected by the one or more patient category selectors (6) and of the one or more ventilation mode selectors (7).

13. The apparatus of claim 1, wherein the controller (4) comprises at least one microprocessor (9).

14. The apparatus of claim 1, wherein the apparatus is further configured to, as a default, have selected an adult patient category and to be in stand-by mode.

15. The apparatus of claim 1, wherein the apparatus is further configured such that, during a ventilation, modifying the ventilation mode requires successively the actuation, by the user, of:

a) the one or more ventilation mode selectors (7) for passing from a first ventilation mode (Modes 1-6) to a desired second ventilation mode (Modes 1-6) compatible with the selected desired patient category, and b) a validation button (19) of the apparatus.

* * * * *